(12) United States Patent
Bortolin et al.

(10) Patent No.: US 9,687,661 B2
(45) Date of Patent: Jun. 27, 2017

(54) SYSTEMS AND METHODS FOR ATTACHING PRE-FABRICATED HEADER CONNECTOR ASSEMBLY TO HOUSING OF IMPLANTABLE ELECTRONIC DEVICE

(71) Applicant: PACESETTER, INC., Sylmar, CA (US)

(72) Inventors: Dino Bortolin, Camarillo, CA (US); Ekaterina Tkatchouk, Sherman Oaks, CA (US); Christopher R. Jenney, Valencia, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 14/839,750

(22) Filed: Aug. 28, 2015

(65) Prior Publication Data

US 2017/0056674 A1    Mar. 2, 2017

(51) Int. Cl.
  *A61B 5/02*     (2006.01)
  *A61N 1/375*    (2006.01)
  *A61B 5/00*     (2006.01)
  *A61B 5/0402*   (2006.01)

(52) U.S. Cl.
  CPC .......... *A61N 1/3752* (2013.01); *A61B 5/0402* (2013.01); *A61B 5/686* (2013.01); *A61B 2562/22* (2013.01)

(58) Field of Classification Search
  CPC .. A61N 1/3752; A61B 5/686; A61B 2562/22; A61B 5/0402
  See application file for complete search history.

(56) References Cited

U.S. PATENT DOCUMENTS

| 4,041,956 | A | 8/1977 | Purdy et al. |
| 5,897,578 | A | 4/1999 | Wiklund et al. |
| 7,083,474 | B1 | 8/2006 | Fleck et al. |
| 7,630,768 | B1 * | 12/2009 | Coffed ................. A61N 1/3752 607/37 |
| 8,140,163 | B1 * | 3/2012 | Daglow ............... A61N 1/3752 607/36 |
| 2002/0128692 | A1 | 9/2002 | Imani et al. |
| 2002/0138114 | A1 | 9/2002 | Gramse |
| 2004/0116976 | A1 | 6/2004 | Spadgenske |
| 2004/0191621 | A1 | 9/2004 | Heller, Jr. |
| 2008/0255631 | A1 | 10/2008 | Sjostedt et al. |
| 2010/0019985 | A1 * | 1/2010 | Bashyam ............. A61B 5/0031 343/873 |

* cited by examiner

*Primary Examiner* — George Manuel

(57) ABSTRACT

Implementations of the present disclosure may take the form of an implantable electronic device such as an implantable pulse generator for administering electrotherapy via an implantable medical lead configured to couple with the implantable pulse generator, or an implantable cardiac monitor. The implantable electronic device includes a housing, a header connector assembly and a sealing member. The header connector assembly includes a connector assembly and a header enclosing the connector assembly. The sealing member is sandwiched between the header connector assembly and the housing.

23 Claims, 15 Drawing Sheets

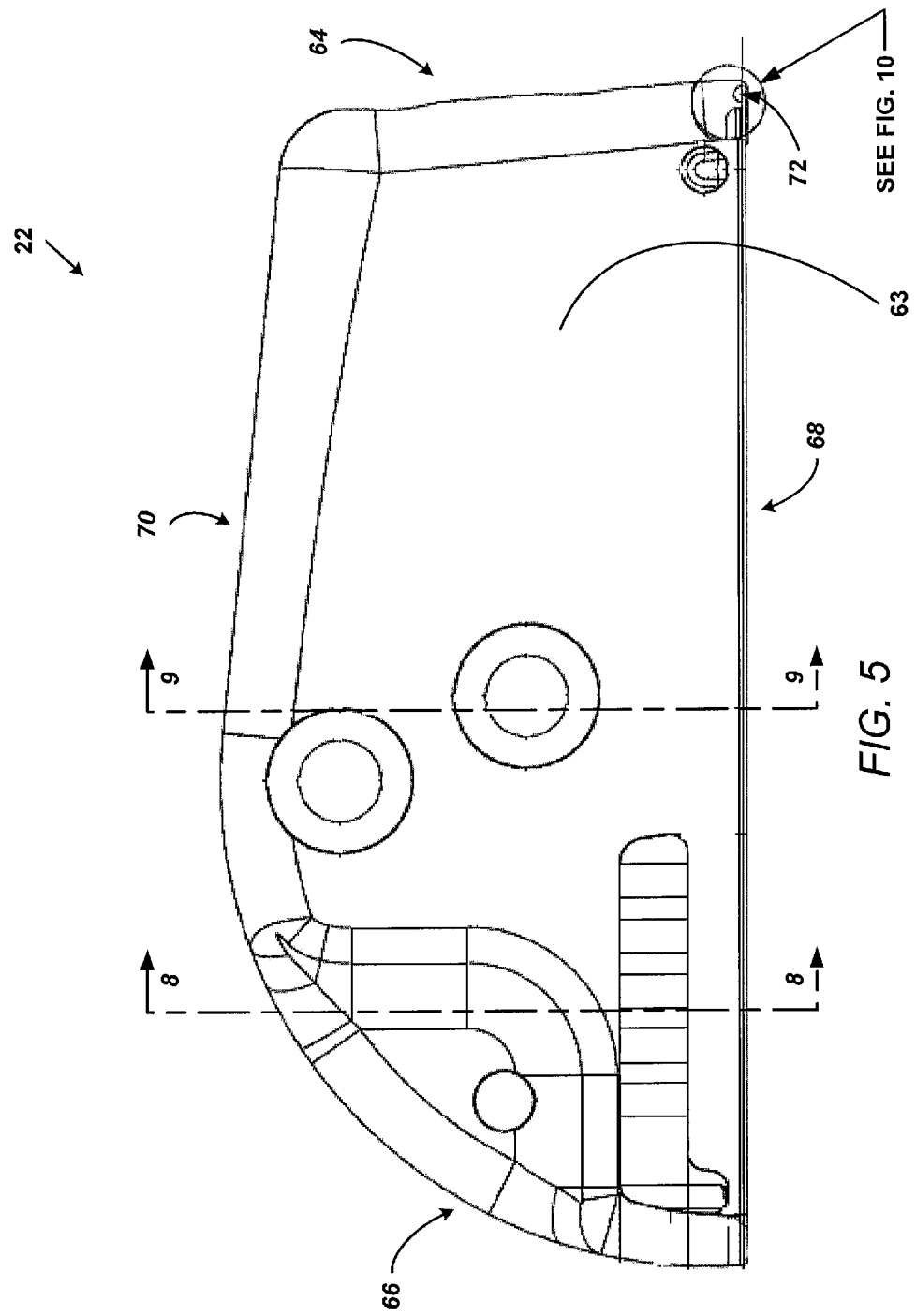

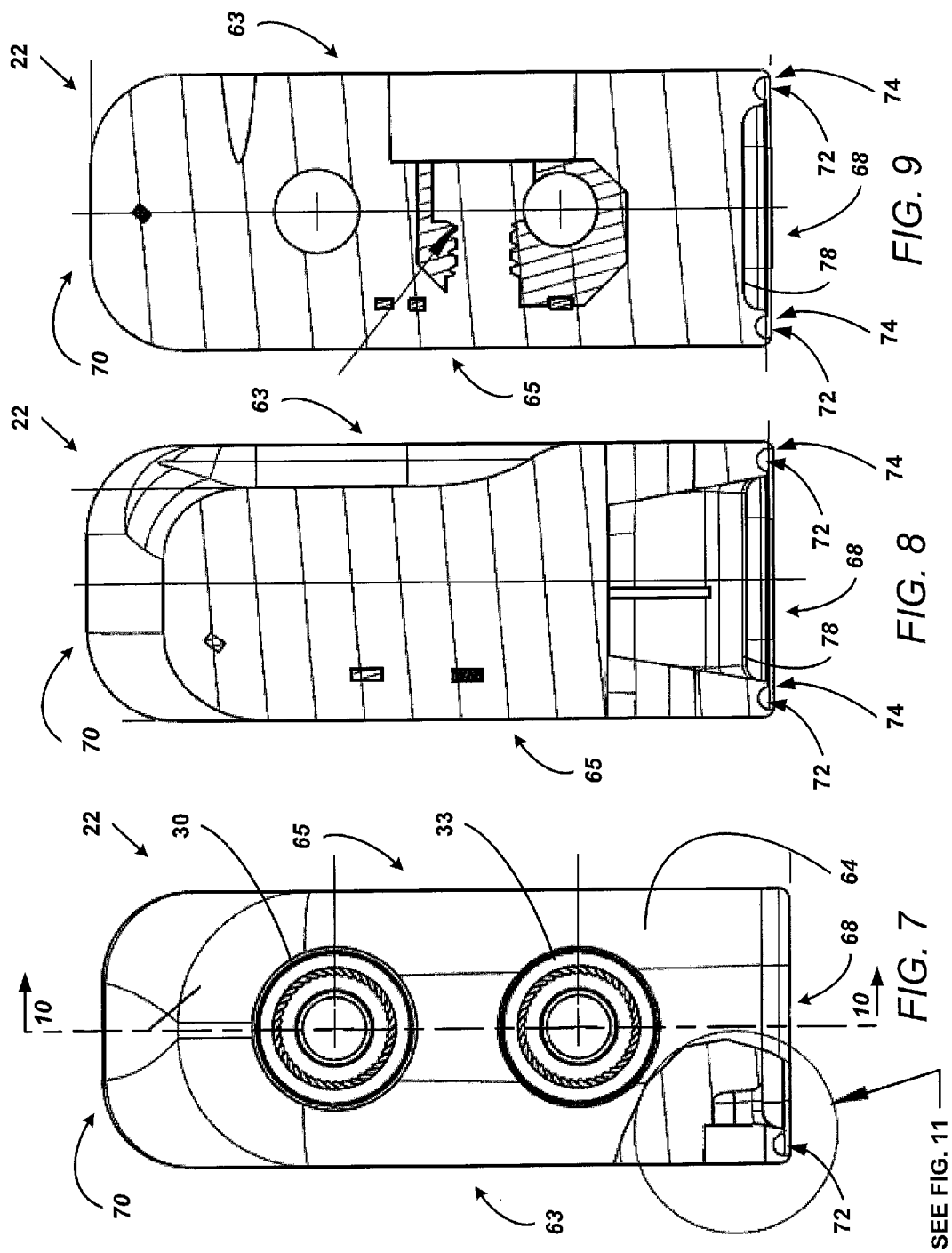

SYSTEMS AND METHODS FOR ATTACHING PRE-FABRICATED HEADER CONNECTOR ASSEMBLY TO HOUSING OF IMPLANTABLE ELECTRONIC DEVICE

FIELD OF THE INVENTION

Aspects of the present invention relate to medical apparatus and methods. More specifically, the present invention relates to systems and methods for attaching a pre-fabricated header connector assembly to a housing of an implantable electronic device such as an implantable pulse generator or implantable cardiac monitor.

BACKGROUND OF THE INVENTION

Implantable pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems, commonly include a housing, feedthrus, and a connector assembly that is enclosed in a header. Electrical stimulation originating in the housing is led to the connector assembly through feedthrus. The connector assembly serves to transmit electrical signals out of the IPG and to a lead electrically connected to the connector assembly, the lead transmitting electrical signals between the IPG and patient tissue.

Other implantable electronic devices such as, for example, implantable cardiac monitors (ICMs) also employ a housing and a header. ICMs are used to monitor heart function or other electrical signals, but do not administer electrotherapy.

Current header casting manufacturing processes and the associated methods of assembling the header and its enclosed connector assembly onto the housing require multiple operations, are skill intensive, and unavoidably time consuming. Connector assemblies are first cast into a header separate from the housing, the header and the connector assembly enclosed therein forming a header connector assembly. The header connector assembly is joined with the housing by injecting a thermosetting polymer (e.g., an epoxy) into an interface between the header connector assembly and the housing, such an injection process being called a backfill process. This backfill process creates attachment and electrical sealing between the header connector assembly and the housing. However, the backfill process nearly mirrors the extensive casting process used to encase the connector assembly in the header to form the header connector assembly, the backfill process involving mold set-up, mold pre-heat, epoxy dispense, epoxy curing, and mold breakdown. The backfill process is not only lengthy, but also expensive due to its many tools and equipment, and necessity for many skilled operators.

Due to the low viscosity characteristics of epoxy used in the backfill process, the epoxy has a tendency to flow into undesired areas. A common cause for rework on implantable electronic devices involves epoxy entering one or more of the lead connector receiving bores of the header connector assembly, thereby forming a barrier to the establishment of critical electrical connections between the electrical terminals of the lead connector ends and the electrical contacts of the connector assembly. Such implantable electronic device rework further extends costs and manufacturing times. Other causes for rework are experienced throughout the casting and backfill processes.

There is a need in the art for systems and methods that reduces the complexity, time, tooling and costs associated with the backfill process.

BRIEF SUMMARY OF THE INVENTION

The devices and methods disclosed herein substantially reduce, if not eliminate completely, costly "backfill" tooling that is traditionally used to capture/retain backfill material in the confines of the header backfill cavity. Irregularities in the housings of implantable electronic device (e.g., IPGs and ICMs) post welding traditionally create leakage resulting in additional processing time, materials and equipment. Creating a groove around the perimeter of the header to receive or retain therein either a pre-formed sealing member, or allow for dispensing of sealing material in the groove to form a sealing member therein, eliminates the need for separate tooling and provides a leak free interface resulting in no additional post processing. The sealing member can be incorporated in various materials used to create a pre-manufactured header. Some non-limiting examples include: two parts epoxies, thermal set polyurethanes and other various polymers used in the manufacturing of implantable electronic device headers such as those employed for an IPG or an ICM.

Depending on the embodiment, the sealing member material used to capture and retain the backfill material can be silicone based in a preformed geometry or can be dispensed directly into a groove on the bottom side of the header. Once the sealing member material is in place in the groove, the header can be assembled to the implantable electronic device housing, and the backfill process can be performed without the need of any additional tooling or post processing.

One implementation of the present disclosure may take the form of an implantable pulse generator for administering electrotherapy via an implantable medical lead configured to couple with the implantable pulse generator. The implantable pulse generator includes a housing, a header connector assembly and a sealing member. The header connector assembly includes a connector assembly and a header enclosing the connector assembly. The sealing member is sandwiched between the header connector assembly and the housing. A similar implementation of the present disclosure can take the form of another implantable electronic device, such as, for example, an implantable cardiac monitor.

In one embodiment, the header connector assembly may include a groove in which the sealing member at least partially resides when sandwiched between the header connector assembly and the housing. For example, the groove may be defined in the header of the header connector assembly.

In another embodiment, a top surface of the housing may include a groove in which the sealing member at least partially resides when sandwiched between the header connector assembly and the housing.

In one embodiment, the sealing member extends along a peripheral boundary of an area of interfacing between the header connector assembly and the housing. For example, the sealing member may extend along the entirety of the peripheral boundary continuous and uninterrupted.

In one embodiment, the implantable pulse generator further includes a backfill material located in a backfill volume defined between a bottom surface of the header connector assembly, a top surface of the housing, and an inner surface of the sealing member.

In one embodiment, the header connector assembly includes a peripheral rim including a groove in which sealing member resides. Alternatively, or additionally, in some embodiments, the housing includes a peripheral rim including a groove in which sealing member resides.

Depending on the embodiment, the sealing member may include at least one of silicone rubber, polyurethane, silicone rubber—polyurethane—copolymer (SPC), or a solvent based adhesive.

Another implementation of the present disclosure may take the form of a method of manufacturing an implantable pulse generator for administering electrotherapy via an implantable medical lead configured to couple with the implantable pulse generator, or a method of manufacturing another implantable electronic device, such as, for example, an implantable cardiac monitor. The method includes: a) sandwiching a sealing member between a housing and a header connector assembly; and b) backfilling between a top surface of the housing, a bottom surface of the header connector assembly, and an inner surface of the sealing member.

In one embodiment, the method further includes and subsequent to step a) and prior to step b), welding components of a connector assembly of the header connector assembly to components of a feedthru of the housing.

In one embodiment of the method, the header connector assembly includes a groove in which the sealing member at least partially resides when sandwiched between the header connector assembly and the housing. A top surface of the housing may include a groove in which the sealing member at least partially resides when sandwiched between the header connector assembly and the housing. Also, the header connector assembly may be pre-manufactured prior to being used to sandwich the sealing member between the housing and header connector assembly.

In one embodiment of the method, the sealing member is a pre-manufactured part having the same geometry as a groove in which the sealing member is received prior to being sandwiched between the header connector assembly and the housing. Also, the sealing member may include at least one of silicone rubber, polyurethane, or silicone rubber—polyurethane—copolymer (SPC).

In another embodiment of the method, the sealing member may be deposited into a groove as a silicone rubber based liquid or gel. The groove is part of at least the header connector assembly or the housing. The silicone based liquid or gel is fully cured before the sealing member is sandwiched between the header connector assembly and the housing.

In yet another embodiment of the method, the sealing member is deposited into a groove as a silicone rubber based liquid or gel. The groove is part of at least the header connector assembly or the housing. The silicone based liquid or gel is not yet fully cured before the sealing member is sandwiched between the header connector assembly and the housing.

In another embodiment of the method, the sealing member is deposited into a groove as a solvent based adhesive. The groove is part of at least the header connector assembly or the housing. The solvent based adhesive is not yet fully cured before the sealing member is sandwiched between the header connector assembly and the housing.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 5 is a side view of a header connector assembly formed from the header of FIGS. 3A and 3B and the connector assembly of FIGS. 4A and 4B, which is enclosed in the header, the header connector assembly being configured to receive and support a sealing member to be sandwiched between a bottom surface of the header connector assembly and a top surface of a housing of an IPG.

FIG. 7 is a connector end view of the header connector assembly of FIG. 5.

FIGS. 8 and 9 are transverse cross sectional elevations of the header connector assembly as respectively taken along section lines 8-8 and 9-9 of FIG. 5.

DETAILED DESCRIPTION

Implementations of the present disclosure involve an implantable electronic device such as an implantable cardiac monitor (ICM) or an implantable pulse generator (IPG). The IPG administers electrotherapy or other neurostimulation via an implantable lead having a lead connector end on a proximal end of the implantable lead. The IPG includes a housing or can and a connector assembly enclosed in a header to form a header connector assembly that is coupled to the housing or can. The header connector assembly has at least one lead connector receiving bore or receptacle that includes electrical contacts of the connector assembly that make electrical contact with corresponding electrical terminals on the lead connector end on the proximal end of the implantable lead when the lead connector end is plugged into or otherwise received in the lead connector receiving bore or receptacle. Via the electrical connection between the corresponding electrical terminals of the lead connector end and the electrical contacts of the lead connector receiving bore, electrical signals can be administered from the IPG and through the lead to patient tissue. Similarly, but in reverse, electrical signals originating in patient tissue can travel via the lead to the IPG to be sensed at the IPG.

The ICM is similar to the IPG in that it also includes a housing or can and a header. However, unlike the IPG, the ICM does not attach to leads and the ICM simply monitors electrical signals and does not administer therapy.

The implantable electronic device configurations and methods of assembly disclosed herein are advantageous for at least the reason that they simplify the backfill process used in the process of attaching the header connector assembly to the housing. Specifically, the implantable electronic devices disclosed herein are configured such that a pre-molded header connector assembly with unique and advantageous backfill retention features reduces the time, tooling, complexity and cost associated with the backfill process. In at least one of the embodiments disclosed herein, the pre-molded header connector assembly with the unique and advantageous backfill retention features substantially reduces, if not entirely eliminates, the need for costly backfill tooling while reducing the likelihood of backfill leakage.

Before beginning a detailed discussion of the assembly of the header and the connector assembly enclosed therein onto the housing, a general discussion is first given regarding features of a common lead connector end at the proximal end of an implantable medical lead followed by a general discussion of the features of an IPG. While following discussion of the implantable electronic device is given in the context on an IPG, it can be readily understood by those of skill in the art that the discussion is applicable to an ICM for the pertinent aspects of this disclosure.

Figure 1:
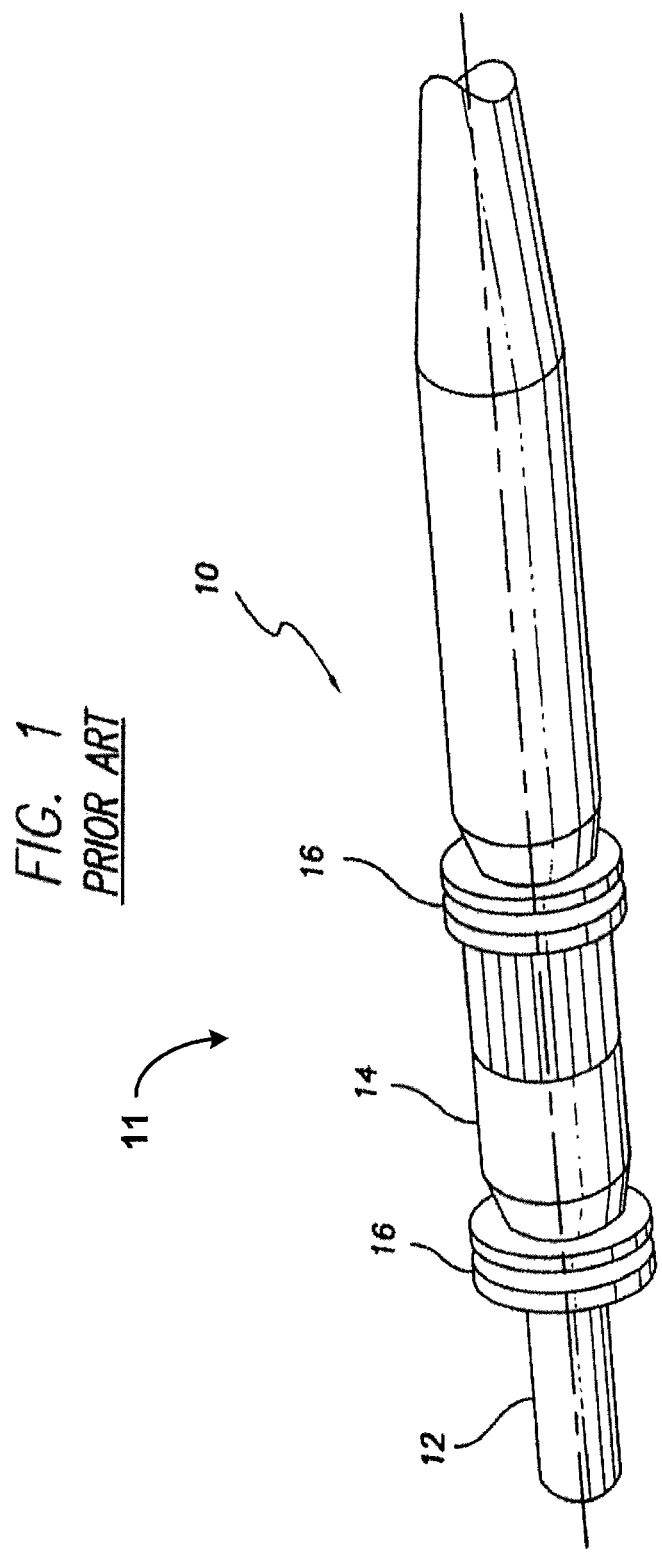
FIG. 1 is an isometric view of a proximal end portion (i.e., lead connector end) of a conventional transvenous bipolar pacing lead.

FIG. 1 shows a proximal end portion 10 of a conventional transvenous, bipolar pacing lead, but is generally representative of any type of implantable lead whether in the cardiac, pain management or other medical treatment space. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, multipolar leads have proximal ends portions that are bifurcated, trifurcated or have other branched configurations. While the lead whose proximal end is shown in FIG. 1 is of the bipolar variety, there are unipolar leads that carry but a single electrode, and multipolar leads that have more than two electrodes.

As is well known in the art, bipolar coaxial leads typically consists of a tubular housing of a biocompatible, biostable insulating material containing an inner multifilar conductor coil that is surrounded by an inner insulating tube. The inner conductor coil is connected to a tip electrode on the distal end of the lead. The inner insulating tube is surrounded by a separate, outer multifilar conductor coil that is also enclosed within the tubular housing. The outer conductor coil is connected to an anodal ring electrode along the distal end portion of the lead. The inner insulation is intended to electrically isolate the two conductor coils preventing any internal electrical short circuit, while the housing protects the entire lead from the intrusion of body fluids. These insulating materials are typically either silicone rubber or polyurethane. More recently, there have been introduced bipolar leads in which multifilar cable conductors contained within multilumen housings are substituted for the conductor coils in order to reduce even further the overall diameter of the lead.

The proximal lead end portion 10 shown in FIG. 1 includes a lead connector end 11 that conforms to the IS-1 standard, comprising a pair of coaxial spaced-apart electrical terminals including a tip terminal 12 and a ring terminal 14. The tip terminal 12 is electrically connected by means of the inner conductor coil to the tip electrode at the distal end of the lead, while the ring terminal 14 is electrically connected to the anodal ring electrode by means of the outer conductor coil. The tip and ring terminals of the lead connector end may each be engaged by a conductive garter spring contact or other resilient electrical contact element in a corresponding lead connector receiving bore of the header, the resilient electrical contact element being carried by a connector assembly enclosed in the header as described below. The lead connector end 11 on the proximal lead end portion 10 further comprises spaced-apart pairs of seal rings 16 for abutting against in a fluid-sealing manner the inner circumferential surface of the lead connector receiving bore of the header, thereby preventing body fluids from reaching the electrical terminals and contacts when the lead connector end 11 is plugged into the corresponding lead connector receiving bore. With the lead connector end 11 of the lead inserted in the lead connector receiving bore of the header and connector assembly, the tip and ring terminals 12 and 14 are electrically coupled via the contacts of the connector assembly and a feedthru to the electronic circuits within the hermetically sealed housing of the IPG (e.g., cardiac pacemaker, ICD, or other implantable tissue stimulation and/or sensing device such as those used in pain management, etc.).

Figure 2:
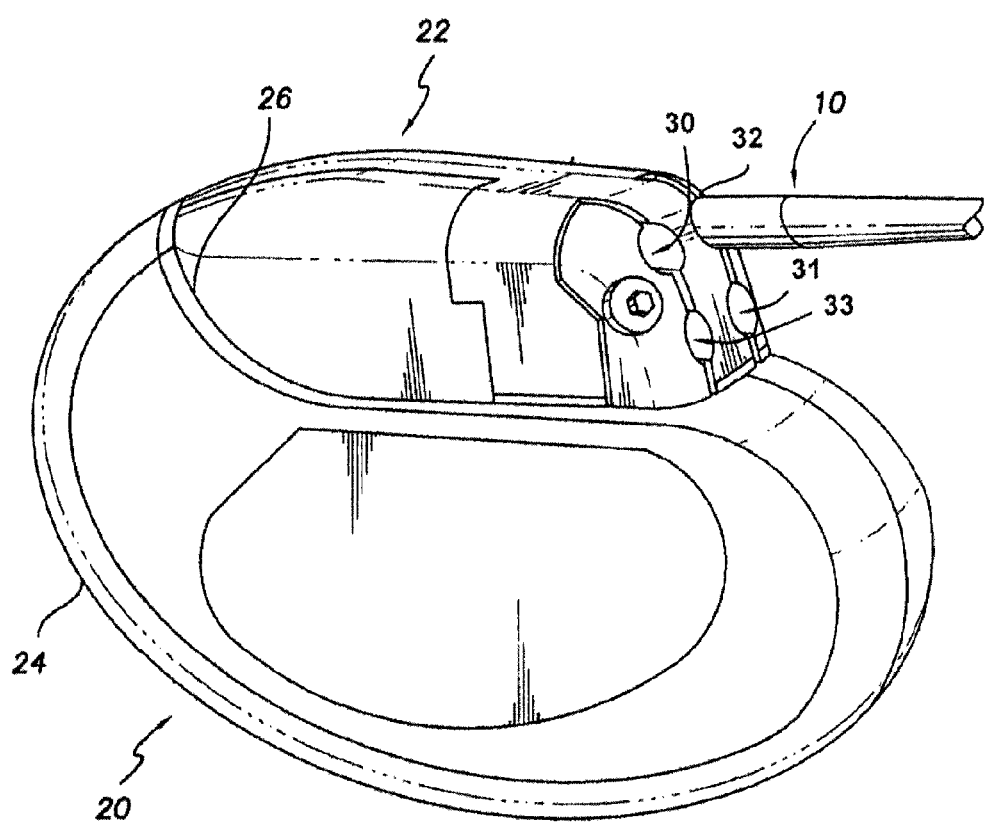
FIG. 2 is an isometric view of a cardiac pacemaker/defibrillator unit (i.e., implantable pulse generator (IPG)) incorporating connector junctions or terminals for communication with one or more electrodes.

FIG. 2 shows a multi-site or multi-chamber cardiac pacemaker/defibrillator unit that is generally representative of any type of IPG 20 incorporating a header connector assembly 22 coupled to a housing 24. The header connector assembly 22 includes a header 40 enclosing a connector assembly 42, both of which are depicted respectively in FIGS. 3A and 3B discussed below. The IPG 20 is of a conventional design, including a hermetically sealed housing 24, which is also known as a can or casing. The housing 24 encloses the electronic components of the IPG 20 with the header connector assembly 22 mounted along a top surface 26 of the housing 24.

FIG. 2 illustrates that, in some embodiments, the header connector assembly 22 may include four or more lead connector receiving bores or receptacles 30, 31, 32 and 33 for receiving the lead connector ends of four implantable leads. FIG. 2 also shows the proximal end portion 10 of a lead, wherein the lead connector end on the proximal end portion 10 of the lead is received in a corresponding receptacle 32. In other embodiments, the header connector assembly 22 includes two receptacles comprising a single pair of receptacles (i.e., receptacles 30 and 33) for receiving the proximal ends of leads such as, for example, conventional bipolar leads and/or conventional cardioverting and/or defibrillating leads.

Figure 3A:
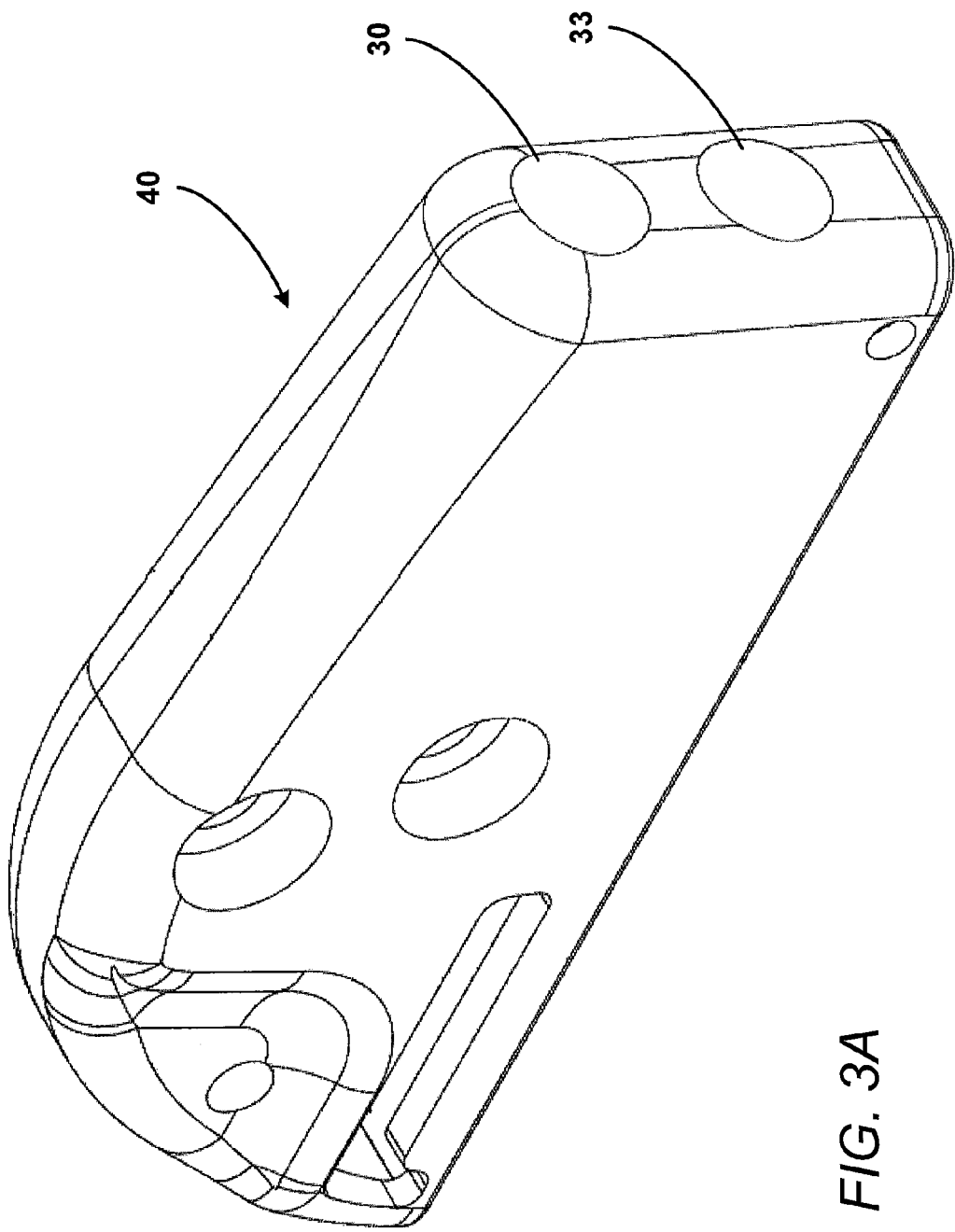
FIGS. 3A and 3B are opposite isometric views of a representative header.
Figure 3B:
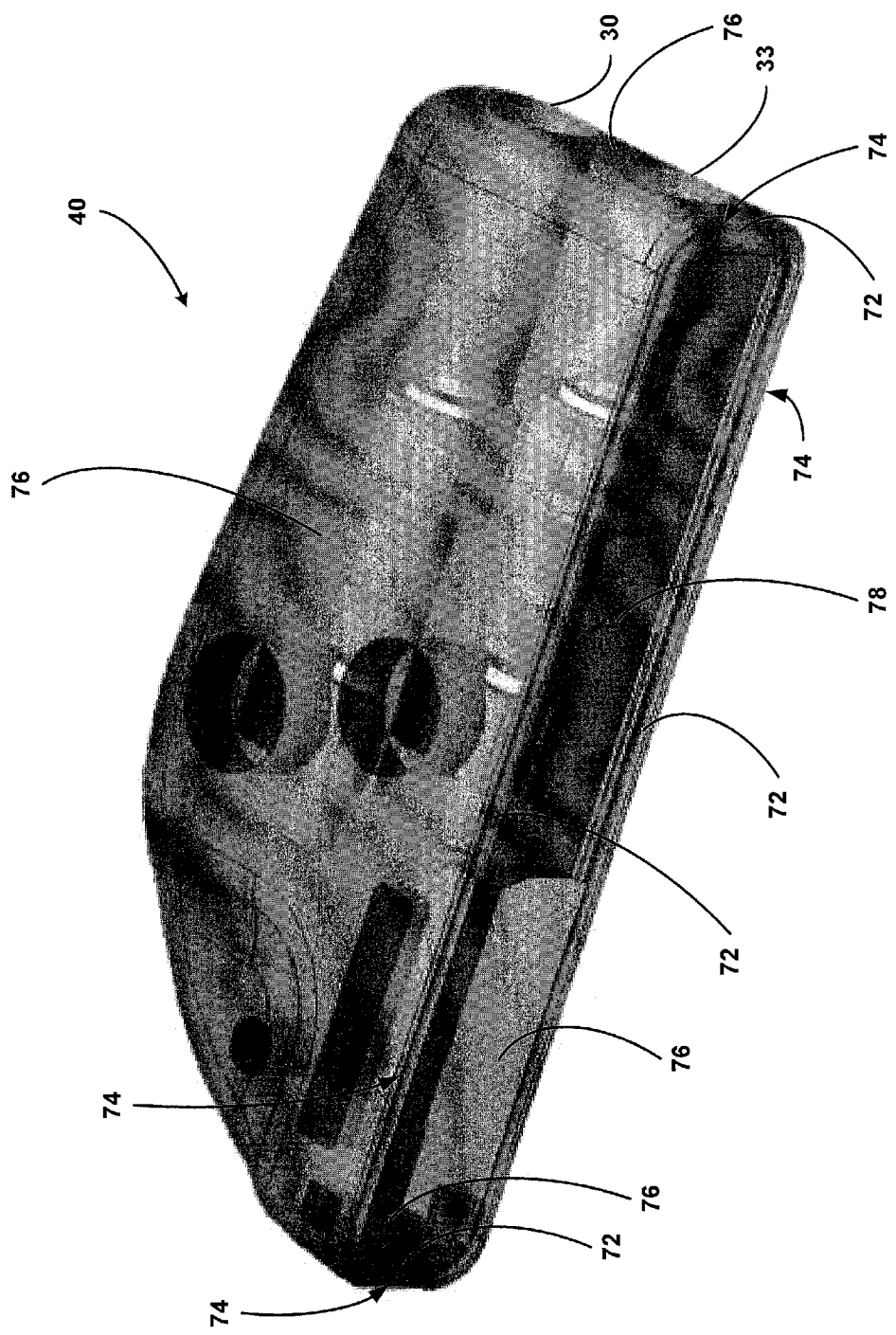
Figure 4A:
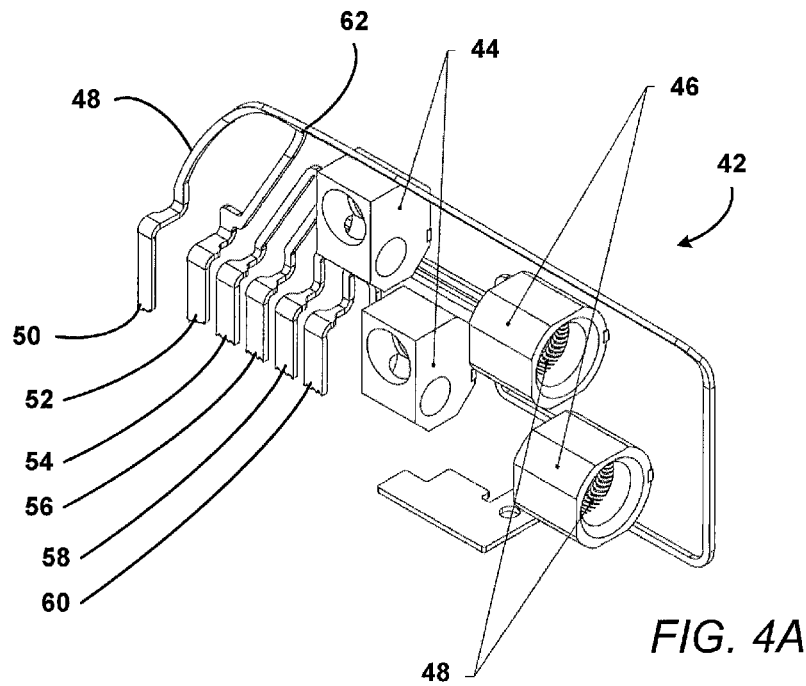
FIGS. 4A and 4B are opposite isometric views of a representative connector assembly used with the header of FIGS. 3A and 3B to form a header connector assembly.
Figure 4B:
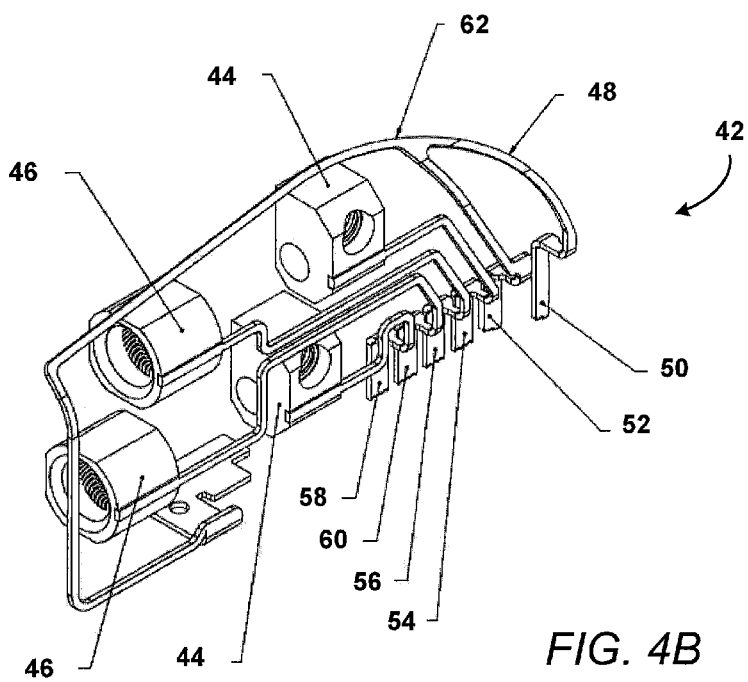

FIGS. 3A and 3B are opposite isometric views of a representative header 40 and FIGS. 4A and 4B are opposite isometric views of a representative connector assembly 42. Unlike the header connector assembly 22 of FIG. 2, the header 40 of FIGS. 3A and 3B only has a single pair of receptacles 30 and 33. However, in other embodiments, the header 40 of FIGS. 3A and 3B may have two or more pairs of receptacles similar to the embodiment of FIG. 2.

As illustrated in FIGS. 4A and 4B, the connector assembly 42 includes tip blocks 44 and ring blocks 46. The ring blocks 46 include spring contacts 48. Each electrical block 44 and 46 of the connector assembly 42 serves as an electrical contact of the connector assembly 42. Thus, as can be understood from FIGS. 1-4B, each tip block 44 is configured to receive and make electrical contact with the tip terminal 12 of a lead connector end 11 received in the corresponding receptacle 30, 33 of the header 40. Similarly, each ring block 46 is configured to receive and make electrical contact with the ring terminal 14 of a lead connector end 11 received in the corresponding receptacle 30, 33 of the header 40. While the connector assembly 42 of FIGS. 4A and 4B is of an IS-1 configuration, other configurations (e.g., IS-4, etc.) are used in other embodiments. While the connector assembly 42 of FIGS. 4A and 4B only depicts two pairs of blocks 44, 46, in other embodiments where the header includes more than a single pair of receptacles 30, 33 (e.g., two pairs of receptacles 30, 31, 32, 33 as indicated in FIG. 2), the connector assembly 42 will have a four pairs of blocks 44, 46.

As shown in FIGS. 4A and 4B, the connector assembly 42 also includes an antenna 48, a an RF anchor tab 50, an RF pin tab 52, an A-tip tab 54, an A-ring tab 56, an RV-ring tab 58, an RV-tip tab 60, and a ribbon carrier 62 and other conductors that extend between the various tabs and their respective electrical contacts of the connector assembly or other components thereof. The various tabs are welded to corresponding terminals extending from circuitry of the IPG 20 contained in the housing 24 of the IPG 20 depicted in FIG. 2 when the header connector assembly 22 is joined with the housing 24 to form the IPG 20. The connector assembly 42 is manufactured of materials and via methods known in the industry. The connector assembly 42 is molded into the header 40 to form the header connector assembly 22 of FIG. 2, which can be considered a first module that is then attached via the backfill process to a second module in the form of the housing 24. In other words, the header connector assembly 22 (i.e., first module) is attached via the backfill process to the housing 24 (i.e., the second module) to form the IPG 20.

A. Header Connector Assembly Having Sealing Member for Sealing against Housing

A sealing member is sandwiched between two IPG modules, namely, the header connector assembly 22 and the housing 24, to form a sealed peripheral boundary extending between the two IPG modules when attached together to form the IPG 20. In one embodiment, the sealing member is supported off of the header 40 of the header connector assembly 22. More specifically, the sealing member is supported off of a side of the header 40 that abuts against the housing 24. When the header connector assembly is abutted against the housing, the sealing member is sandwiched against the opposed abutting surfaces of the header connector assembly and the housing, thereby forming a fluid-tight seal at the seam between the header connector assembly and the housing. This fluid tight seal substantially reduces, if not eliminates, the need for expensive, complex and time consuming backfill tooling typically used to capture/retain backfill material in the confines of a header backfill cavity.

Figure 6:
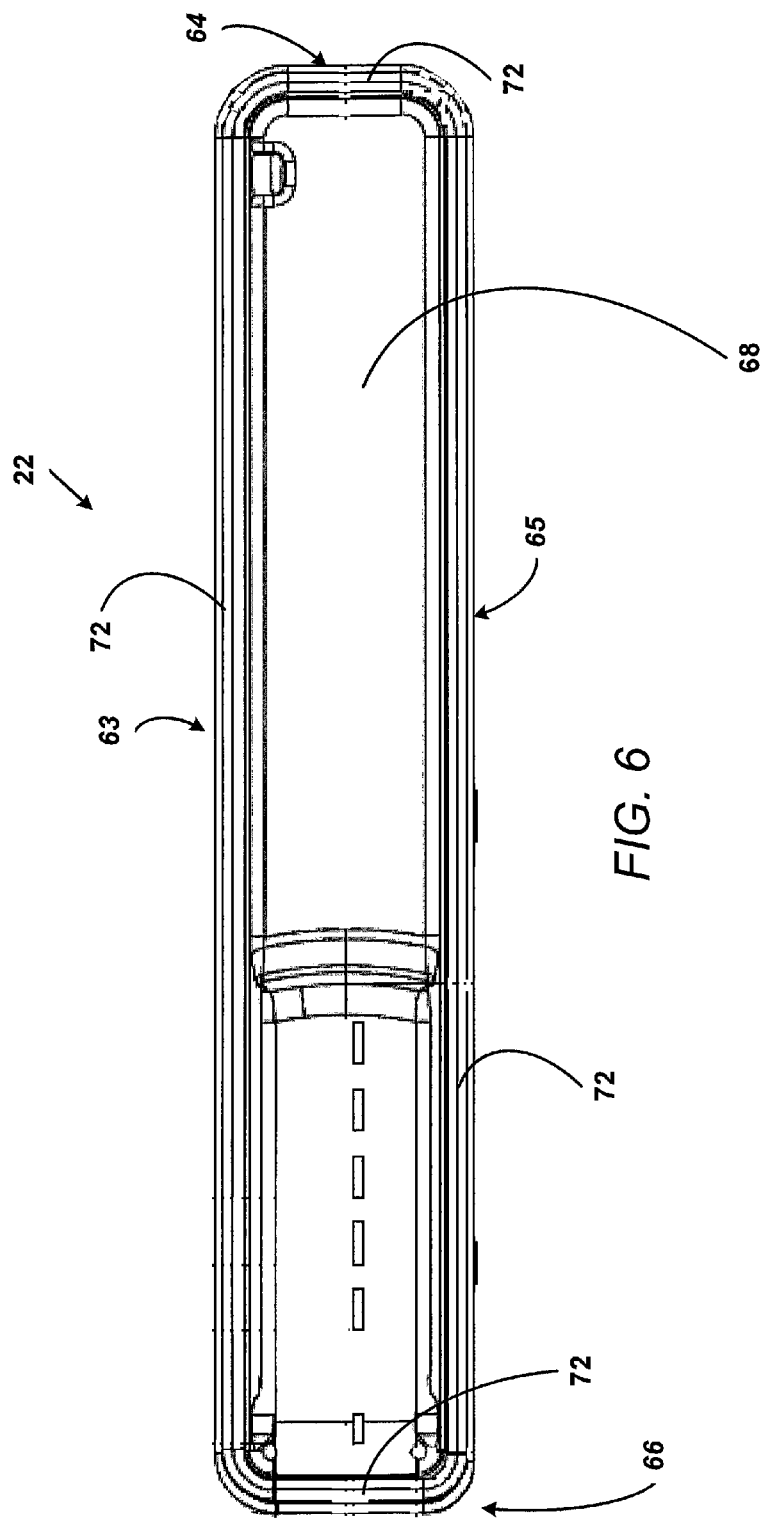
FIG. 6 is a bottom plan view of the header connector assembly of FIG. 5.

To begin a detailed discussion of the sealing member and the associated attachment system and method, reference is made to FIGS. 5, 6 and 7, which are, respectively, a side view, bottom plan view, and connector end view of a header connector assembly 22 configured to receive and support the sealing member. The header connector assembly 22 is formed from the header 40 of FIGS. 3A and 3B and the connector assembly 42 of FIGS. 4A and 4B. As discussed above, the connector assembly is enclosed in the header. The header connector assembly 22 is configured to receive and support a sealing member to be sandwiched between a bottom surface of the header connector assembly and a top surface of a housing of an IPG.

As shown in FIGS. 5-7, the header connector assembly 22 includes opposite sides 63, 65, a connector end 64 and a back end 66 opposite the connector end, a bottom 68 and a top 70 opposite the bottom. Lead connector receiving bores or receptacles 30 and 33 daylight at the connector end 64, and the bottom 68 is configured to abut against a top surface 26 of the housing 24, as can be understood from FIG. 2.

Figure 10:
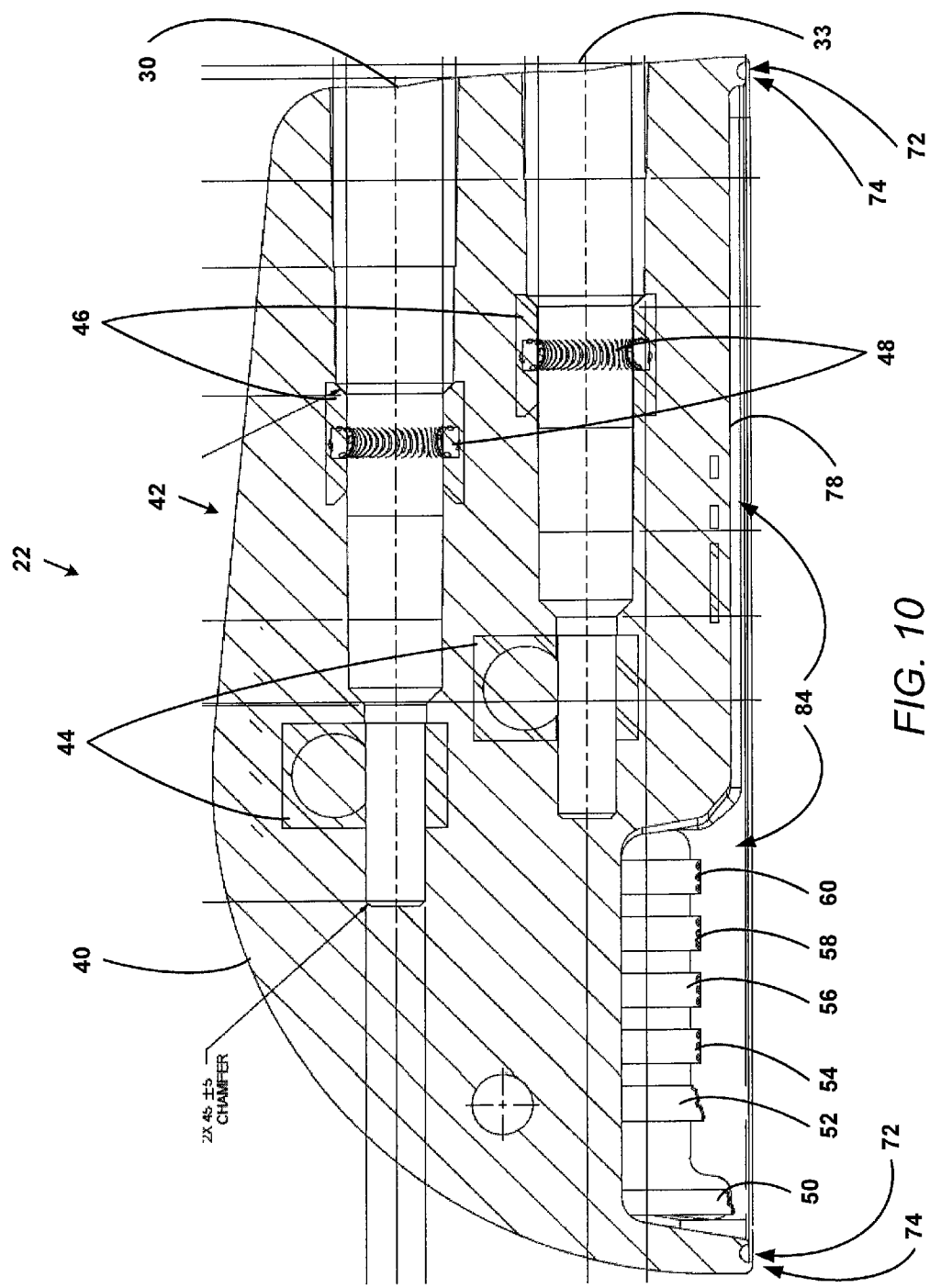
FIG. 10 is a longitudinal cross sectional elevation of the header connector assembly as taken long section line 10-10 of FIG. 7.

FIGS. 8 and 9 are transverse cross sectional elevations of the header connector assembly 22 as respectively taken along section lines 8-8 and 9-9 of FIG. 5, and FIG. 10 is a longitudinal cross sectional elevation of the header connector assembly as taken long section line 10-10 of FIG. 7. The various components 44, 46, 48, 50, 52, 54, 56, 58, 60 of the connector assembly 42, as discussed above in detail with respect to FIGS. 4A and 4B, can be seen in FIGS. 8-10 as being encased in the material of the header 40 to form header connector assembly 22.

As can be understood from FIGS. 5-10, a groove 72 extends along the entirety of the outer peripheral boundary, just radially inward of the outer edge of the bottom 68 of the header connector assembly 22. As can be understood from FIG. 3B, the groove 72 is defined in a bottom projecting rim 74 of the exterior wall structure 76 of the header 40. Both the bottom projecting rim 74 and the groove 72 defined therein extend uninterrupted and continuous about the outer peripheral boundary of the bottom of the header connector assembly. The bottom rim 74 projects downward from an adjacent bottom planar surface 78 of the header 40. The bottom planar surface 78 can be said to be upwardly recessed relative to the peripheral bottom rim 74 that surrounds the bottom planar surface 78.

Figure 11:
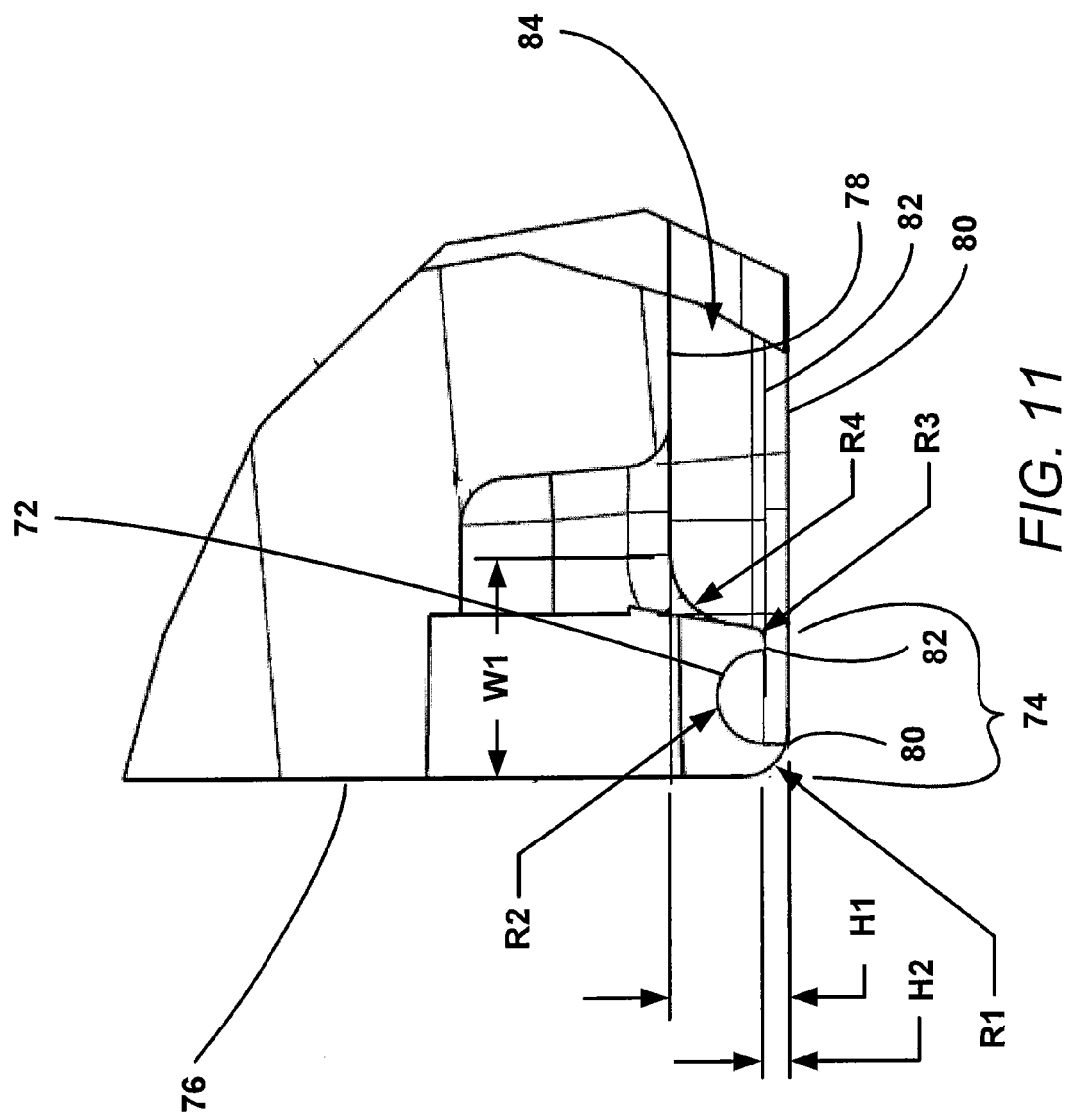
FIGS. 11 and 12 are enlarged views of a corner region of the header connector assembly that is encircled in FIGS. 5 and 7, respectively, wherein the encircled region of the header connector assembly has its exterior wall broken away to show the groove and bottom edge hidden inside.
Figure 12:
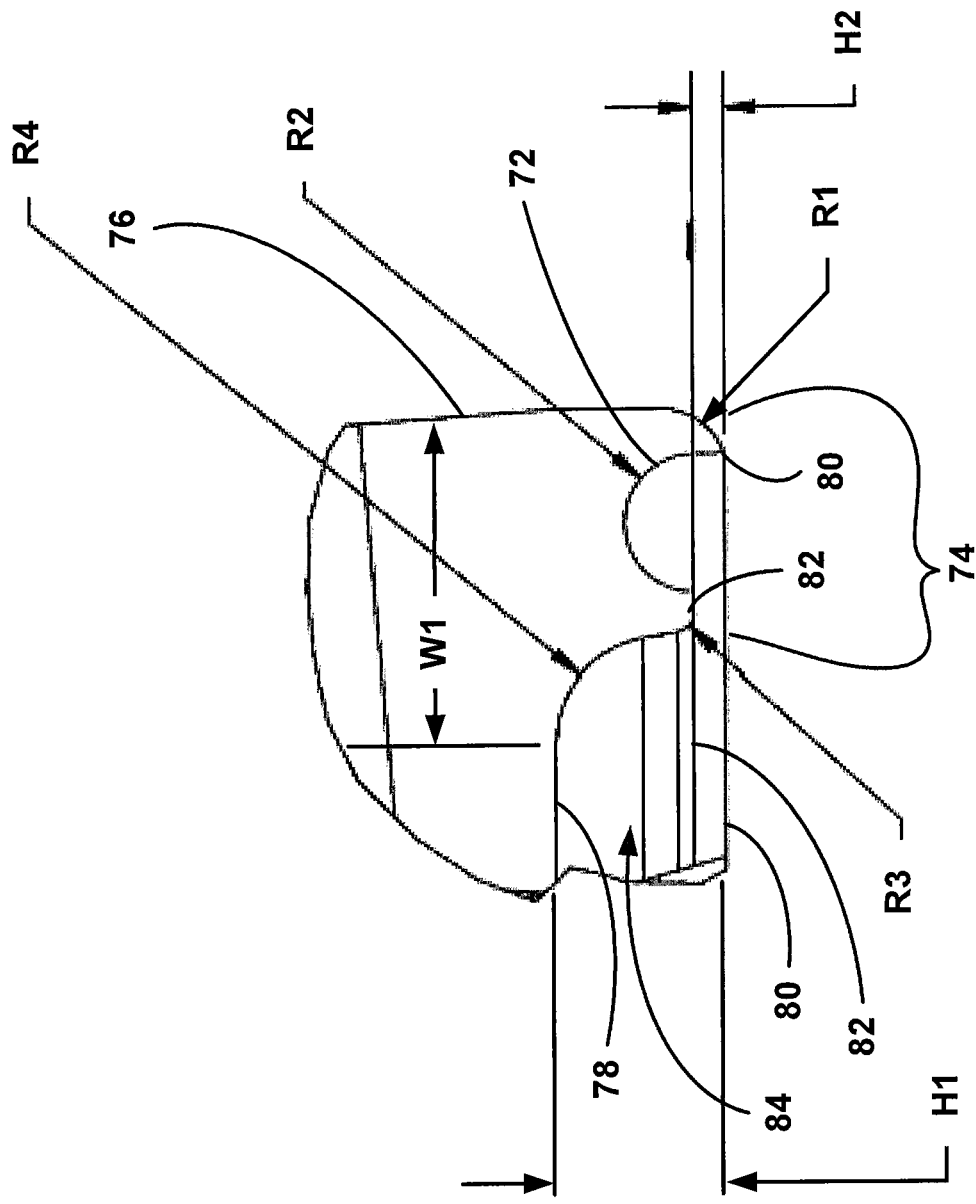

FIGS. 11 and 12 are enlarged views of a corner region of the header connector assembly 22 that is encircled in FIGS. 5 and 7, respectively, wherein the encircled region of the header connector assembly has its exterior wall broken away to show the groove 72 and bottom rim 74 hidden inside. As illustrated in FIGS. 11 and 12, and as can also be understood from FIGS. 3B, 8 and 9, a bottom peripheral rim 74 has an outer edge 80 and an inner edge 82 inward from the outer edge 80 and across the groove 72 from the outer edge 80. The outer edge 80 is defined by an intersection between the arcuate surface of the groove 72 and an arcuate surface of radius R1 that transitions from the outer edge 80 to the outer wall surface 76. The arcuate surface of the groove 72 has a radius of R2.

The inner edge 82 is defined by an intersection between the arcuate surface of the groove 72 and an arcuate surface of radius R3 that transitions from the inner edge 82 to another arcuate surface of radius R4 that transitions to the bottom planar surface 78, which is perpendicular to the outer wall surface 76. The outer edge 80 projects downward a height H1 from the bottom planar surface 78, and the inner edge 82 is recessed upward relative to the outer edge 80 a height H2. Thus, the bottom rim 74 formed by outer edge 80, inner edge 82 and the arcuate transitions having radii R1, R3 and R4 can be said to have inner and outer projective heights H1 and (H1-H2) relative to the bottom planar surface 78.

Also, the bottom rim 74 formed by outer edge 80, inner edge 82 and the arcuate transitions having radii R1, R3 and R4 can be said to have a width W. As can be understood from FIGS. 3B and 10, when the header connector assembly 22 is coupled with the housing 24 as depicted in FIG. 2, the bottom rim 74, the bottom planar surface 78 and the top surface 26 of the housing 24 combine to define an enclosed backfill void 84 in which a backfill material can be injected during the backfill process.

In one embodiment, the dimensions indicated in FIGS. 11 and 12 will be as follows: height H1 will be 0.248 inch plus or minus approximately 0.005 inch; height H2 will be 0.004 inch plus or minus approximately 0.001 inch; width W1 will be 0.434 inch plus or minus 0.005 approximately inch; radius R1 will be 0.01 inch plus or minus approximately 0.002 inch; radius R2 will be 0.01 inch plus or minus approximately 0.002 inch; radius R3 will be 0.003 inch plus or minus approximately 0.001 inch; and radius R4 will be 0.015 inch plus or minus approximately 0.005 inch.

While the embodiment depicted in FIGS. 11 and 12 illustrates a groove 72 and associated surrounding structure wherein the groove 72 has a semi-circular cross-section, the groove and the associated surrounding structure having the above-noted dimensions, in other embodiments, those dimensions may smaller or larger than those indicated. Also, the shapes of the groove and associated surrounding structure may differ from those depicted in FIGS. 11 and 12. For example, the groove 72 may have a rectangular, triangular, octagonal, hexagonal, or other cross-sectional shape.

Figure 13:
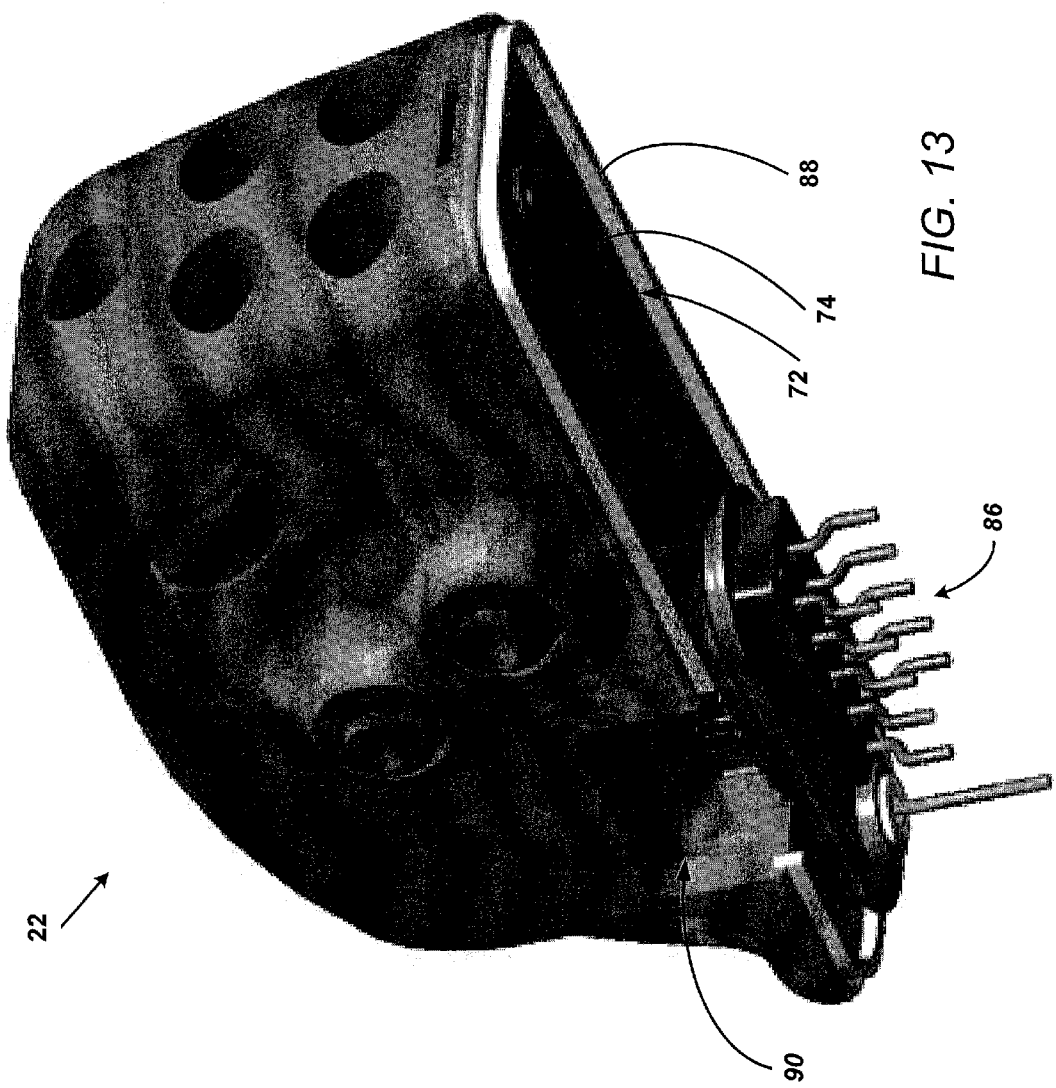
FIG. 13 is a bottom isometric view of the header connector assembly with a feedthru of the housing also shown as attached to corresponding components of the connector assembly, the sealing member being received in the groove defined in the bottom projecting rim of the header connector assembly.

As shown in FIG. 13, which is a bottom isometric view of the header connector assembly 22 with a feedthru 86 of the housing 24 also shown as attached to corresponding components of the connector assembly 42, the sealing member 88 is received in the groove 72 defined in the bottom projecting rim 74 of the header connector assembly 22. In some embodiments, as can be understood from FIG. 3B, the groove 72, and also any sealing member 88 contained therein, extend continuous and uninterrupted about the entirety of the peripheral boarder edge of the header connector assembly 22. In other embodiments, as depicted in FIG. 13, the groove 72 and the sealing member 88 contained therein extend continuous and uninterrupted about the peripheral boarder edge of the header connector assembly 22, except at certain access breaks 90 in the groove 72, sealing member 88 and wall surface 76, such access breaks 90 being available to access welding locations between the feedthru 86 and corresponding components of the connector assembly 42.

Figure 14:
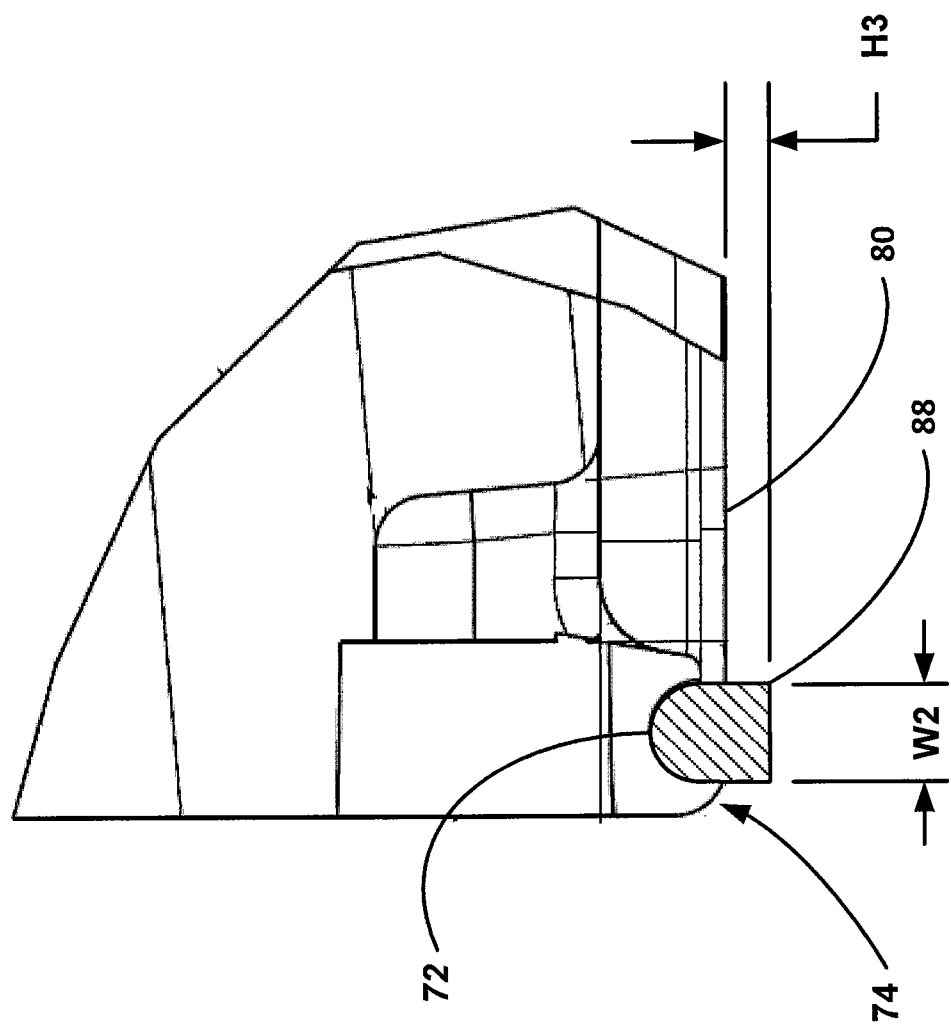
FIGS. 14 and 15 are the same respective views as FIGS. 11 and 12, except now showing the sealing member received in the groove of the bottom projecting rim.
Figure 15:
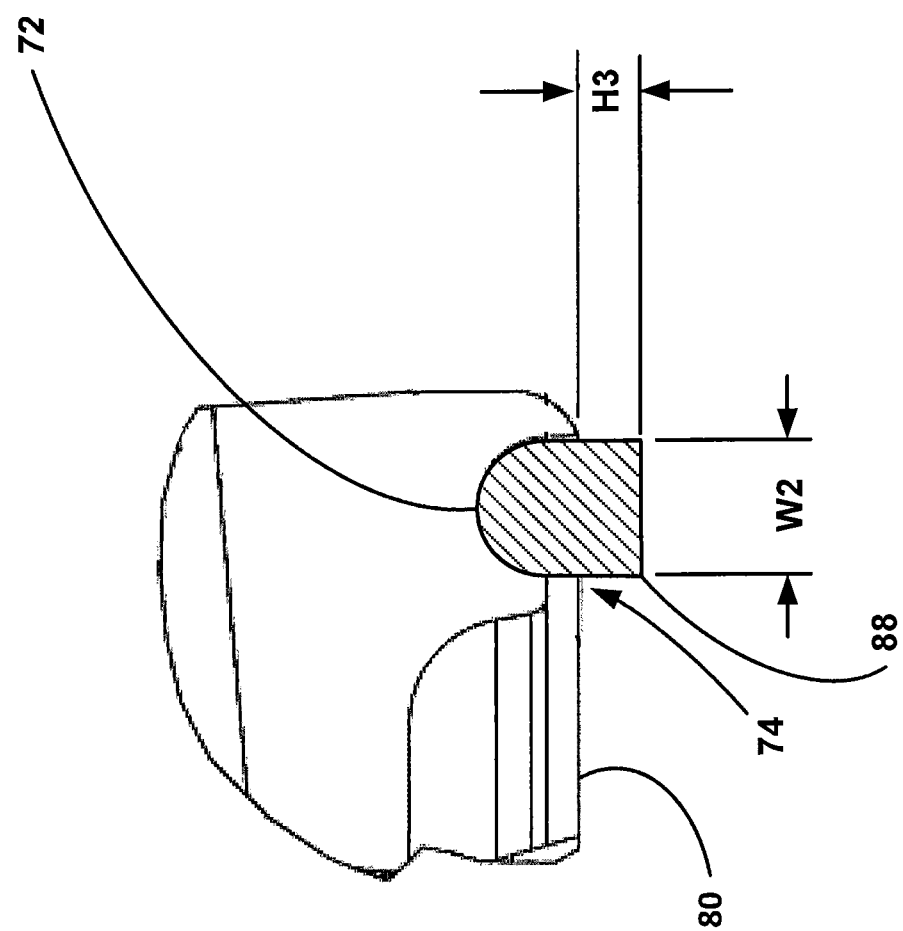

As illustrated in FIGS. 14 and 15, which are the same respective views as FIGS. 11 and 12, except now showing the sealing member 88 received in the groove 72 of the bottom projecting rim 74, the sealing member 88 may have an upper arcuate end that has a mirror radius that matches the radius R2 (see FIGS. 11 and 12) of the groove 72 such that the sealing member 88 fully occupies the groove 72 and the mirrored arcuate surfaces of the sealing member and the groove abut in mating surface contact. As can be understood from FIGS. 14 and 15, the lower portion of the sealing member 88 may have a cross sectional shape that is generally rectangular or have another cross sectional shape such as, for example, oval, square, triangular, etc. The height of the sealing member 88 is sufficient such that it downwardly projects a height H3 beyond the outer edge 80 of the bottom projecting rim 74 when the sealing member is fully seated in the groove 72. The sealing member 88 also has a width W2.

In one embodiment, the dimensions indicated in FIGS. 14 and 15 will be as follows: height H3 will be 0.010 inch plus or minus approximately 0.002 inch; and width W2 will be 0.02 inch plus or minus 0.005 approximately inch.

While the embodiment depicted in FIGS. 14 and 15 illustrates a sealing member 88 having a combination rectangular and semi-circular cross-section, the sealing member having the above-noted dimensions, in other embodiments, those dimensions may smaller or larger than those indicated. Also, the shape may differ from that depicted in FIGS. 11 and 12. For example, the sealing member 88 may have a fully rectangular cross-sectional shape, a fully circular cross-sectional shape, or a triangular, octagonal, hexagonal, or other cross-sectional shape.

While the groove 72 and the rim 74 in which it is defined are discussed above as being part of the header connector assembly 22, and more specifically, as part of the header 40 of the header connector assembly, in other embodiments, the groove and its rim can be part of the top surface 26 of the housing 24 and similarly configured to receive the sealing member 88. In yet other embodiments, a groove 72 and its rim 74 can be located on both the top surface 26 of the housing 24 and the bottom surface of the header connector assembly 22 or its header 40, both of such groove and rim combinations being oppositely positioned relative to each other when the header connector assembly and housing are abutted against each other and both of such groove and rim combinations being configured to receive the sealing member. While any of the aforementioned embodiments as discussed as having a rim 74 in which a groove 72 is defined, in some embodiments, the rim 74 will be absent and the groove 72 will simply be defined in a bottom surface of the header connector assembly or in a top surface 26 of the housing.

The sealing member 88 acts like a gasket or seal between the header connector assembly 22 and the housing 24 of the IPG 20 and is part of the final product forming the IPG 20. In a first manufacturing embodiment, the sealing member 88 is a pre-manufactured part having the same geometry as the groove 72. This pre-manufactured sealing member 88 is placed into the groove 72 as indicated in FIGS. 13-15. In such an embodiment, the pre-manufactured sealing member 88 may be made of an elastomer or other appropriate sealing materials. For example, the pre-manufactured sealing member 88 may be made of silicone rubber, thermoplastic polyurethane (TPU), polycarbonate-polyurethane (PCU), polyurethane, silicone rubber polyurethane copolymer (SPC), polyolefin, or other biostable and biocompatible materials. In other words, the pre-manufactured sealing member 88 may be made of at least one of a silicone elastomer, a thermoplastic elastomer, or other appropriate materials. Once the sealing member has been placed in the groove, the header connector assembly 22 is clamped together with the housing 24, and the components of the connector assembly 42 are resistance or laser welded to the corresponding components of the housing feedthru. The backfill material is then introduced into the backfill cavity 84, after which the backfill material is allowed to cure before the IPG goes to final processing.

In a second manufacturing embodiment, the sealing member 88 is deposited into the groove 72 as a silicone rubber based liquid or gel via manual delivery or an automated dispensing machine. This silicone rubber liquid or gel material is then allowed to cure to result in a gasket or seal similar in configuration to the pre-manufactured part discussed immediately above with respect to the first manufacturing embodiment. Once the sealing member has been fully cured within the groove, the header connector assembly 22 is clamped together with the housing 24, and the components of the connector assembly 42 are resistance or laser welded to the corresponding components of the housing feedthru. The backfill material is then introduced into the backfill cavity 84, after which the backfill material is allowed to cure before the IPG goes to final processing.

In a third manufacturing embodiment, the sealing member 88 is deposited into the groove 72 as a silicone rubber based liquid or gel via manual delivery or an automated dispensing machine. Before the sealing member has fully cured within the groove, the header connector assembly 22 is clamped together with the housing 24. Once the sealing member has finally cured, the components of the connector assembly 42 are resistance or laser welded to the corresponding components of the housing feedthru. The backfill material is then introduced into the backfill cavity 84, after which the backfill material is allowed to cure before the IPG goes to final processing. By sandwiching the uncured sealing member between the header connector assembly and the housing and allowing the sealing member to then cure, the sealing member provides an added level of adhesion between the header connector assembly and the housing over that provided by a simple backfill process.

In still another embodiment, a solvent based adhesive is made by dissolving a raw resin (e.g., thermoplastic polyurethanes (TPU), polycarbonates (PC), polyurethane, silicone-polyurethane copolymer (SPC), polyolefin, or etc.) in a corresponding organic highly polar solvent (e.g., N,N-dimethylformamide (DMF), tetrahydrofuran(THF), N,N-dimethyl acetamide, dimethylsulfoxide (DMSO), Dimethylacetamide (DMAC), Acetone, or etc.). Such resins may be employed in the manufacturing of a polymer based IPG headers. The solvent based adhesive can be prepared at different concentrations of the resin in order to achieve a predetermined viscosity that will allow the adhesive to flow easily from an automated dispensing machine or by hand into the groove 72. Once the adhesive is occupying the groove 72, the adhesive can then cure by solvent evaporation. The header connector assembly and the housing are attached just before the complete solvent evaporation takes place. The solvent based adhesive cures in place into the sealing member 88 much like occurs with respect to the sealing member discussed above with respect to the second or third manufacturing embodiments. However, the resulting sealing member provides higher tensile strength, ductility, and hardness in comparison to silicone rubbers. The solvent based adhesive will also achieve a higher bonding strength with titanium surfaces. Once the sealing member has finally cured, the components of the connector assembly 42 are resistance or laser welded to the corresponding components of the housing feedthru. The backfill material is then introduced into the backfill cavity 84, after which the backfill material is allowed to cure before the IPG goes to final processing.

Figure 16:
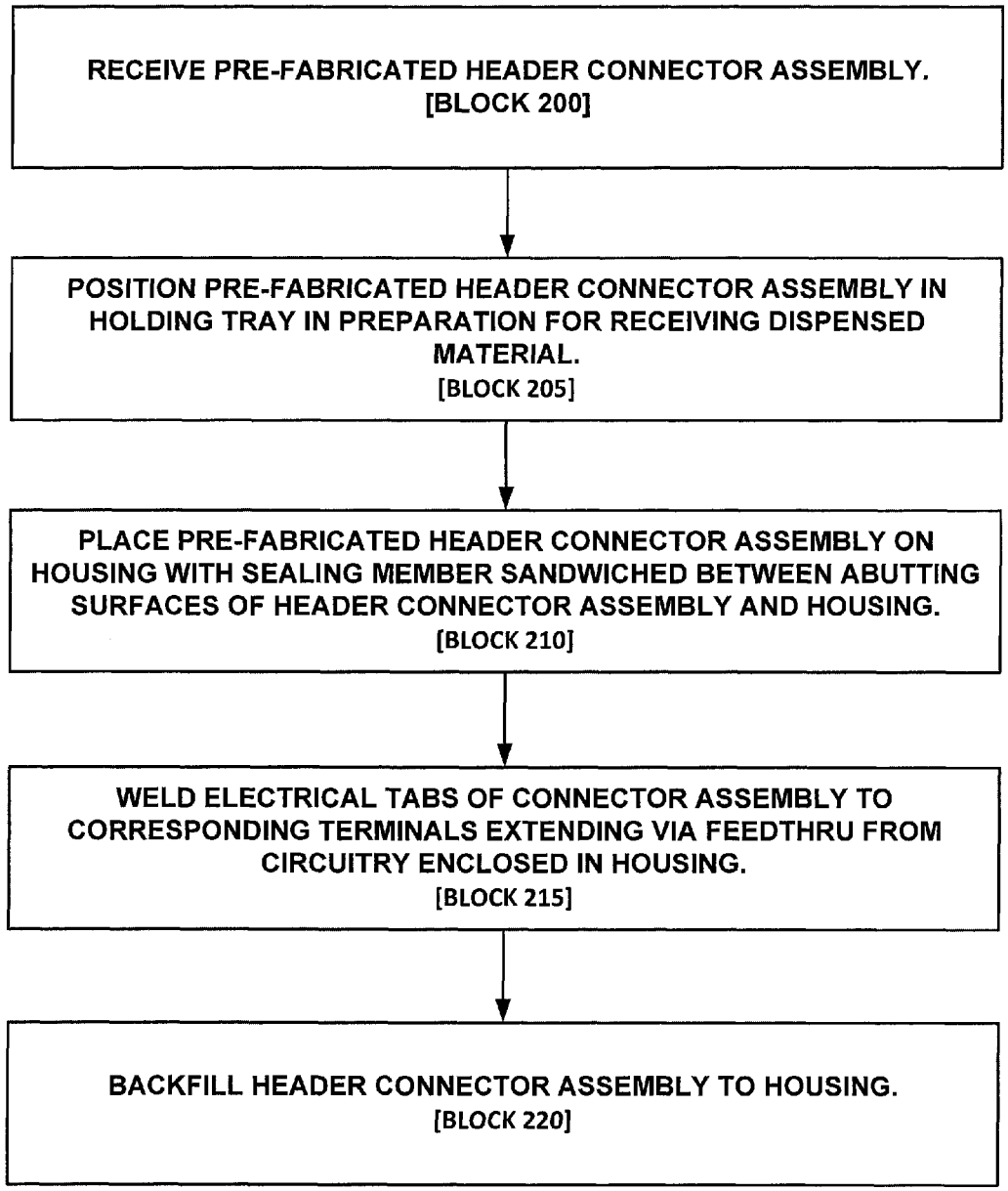
FIG. 16 is a flow chart illustrating a method of manufacturing an IPG, wherein the method employs a sealing member sandwiched between a header connector assembly and a housing of the IPG.

As can be understood from FIG. 16 in view of the four manufacturing embodiments, a pre-fabricated header connector assembly 22 is provided [block 200]. The pre-fabricated header connector assembly is placed in a holding tray in preparation for receiving dispensed material [block 205]. The pre-fabricated header connector assembly is placed on the housing with the sealing member 88 located in the groove 72 and sandwiched between the abutting surfaces of the header connector assembly 22 and the housing 24 [block 210]. The electrical tables of the connector assembly are welded to the corresponding terminals extending via the feedthru from the IPG circuitry enclosed in the housing [block 215]. Backfill is then delivered between the header connector assembly and the housing to join the two IPG modules together in forming the IPG [block 220].

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. An implantable electronic device comprising:
  a housing having a top surface;
  a header connector assembly comprising a connector assembly and a header enclosing the connector assembly, the header connector assembly having a bottom surface; and
  a sealing member formed into an elongated body having an inner surface, the sealing member insertable between the header connector assembly and the housing, the elongated body of the sealing member extending along a peripheral boundary of an area interfacing between the header connector assembly and the housing, an assembly of the housing, the header connector assembly, and the sealing member creating a backfill volume defined by the top surface of the housing, the bottom surface of the header connector assembly, and the inner surface of the elongated body.

2. The implantable electronic device of claim 1, wherein the header connector assembly comprises a groove in which the sealing member at least partially resides when inserted between the header connector assembly and the housing.

3. The implantable electronic device of claim 2, wherein the groove is defined in the header of the header connector assembly.

4. The implantable electronic device of claim 1, wherein the top surface of the housing comprises a groove in which the sealing member at least partially resides when inserted between the header connector assembly and the housing.

5. The implantable electronic device of claim 1, wherein the sealing member extends along the entirety of the peripheral boundary continuous and uninterrupted.

6. The implantable electronic device of claim 1, further comprising a backfill material located in the backfill volume.

7. The implantable electronic device of claim 1, wherein the header connector assembly comprises a peripheral rim including a groove in which sealing member resides.

8. The implantable electronic device of claim 1, wherein the housing comprises a peripheral rim including a groove in which sealing member resides.

9. The implantable electronic device of claim 1, wherein the sealing member comprises at least one of a scone elastomer, a thermoplastic, elastomer, or a solvent based adhesive.

10. The implantable device of claim 1, wherein the implantable electronic device comprises an implantable pulse generator for administering electrotherapy via an implantable medical lead configured to couple with the implantable pulse generator.

11. The implantable device of claim 1, wherein the implantable electronic device comprises an implantable cardiac monitor.

12. A method of manufacturing an implantable electronic device, the method comprising:
   a) sandwiching a sealing member having an elongated body between a housing and a header connector assembly, the elongated body of the sealing member extending along a peripheral boundary of an area interfacing between the header connector assembly and the housing; and
   b) backfilling between a top surface of the housing, a bottom surface of the header connector assembly, and an inner surface of the elongated body of the sealing member with a backfill material, the sealing member preventing leaking of the backfill material.

13. The method of claim 12, further comprising and subsequent to step a) and prior to step b), welding components of a connector assembly of the header connector assembly to components of a feedthru of the housing.

14. The method of claim 12, wherein the header connector assembly comprises a groove in which the sealing member at least partially resides when sandwiched between the header connector assembly and the housing.

15. The method of claim 12, wherein a top surface of the housing comprises a groove in which the sealing member at least partially resides when sandwiched between the header connector assembly and the housing.

16. The method of claim 12, wherein the header connector assembly is pre-manufactured prior to being used to sandwich the sealing member between the housing and header connector assembly.

17. The method of claim 12, wherein the sealing member is a pre-manufactured part having the same geometry as a groove in which the sealing member is received prior to being sandwiched between the header connector assembly and the housing.

18. The method of claim 17, wherein the sealing member comprises at least one of a silicone elastomer, a thermoplastic elastomer, or a solvent based adhesive.

19. The method of claim 12, wherein the sealing member is deposited into a groove as a silicone rubber based liquid or gel, the groove being part of at least the header connector assembly or the housing, the scone based liquid or gel being fully cured before the sealing member is sandwiched between the header connector assembly and the housing.

20. The method of claim 12, wherein the sealing member is deposited into a groove as a silicone rubber based liquid or gel, the groove being part of at least the header connector assembly or the housing, the silicone based liquid or gel not yet being fully cured before the sealing member is sandwiched between the header connector assembly and the housing.

21. The method of cam 12, wherein the sealing member is deposited into a groove as a solvent based adhesive, the groove being part of at least the header connector assembly or the housing, the solvent based adhesive not yet being fully cured before the sealing member is sandwiched between the header connector assembly and the housing.

22. The method of claim 12, wherein the implantable electronic device comprises an implantable pulse generator for administering electrotherapy via an implantable medical lead configured to couple with the implantable pulse generator.

23. The method of claim 12, wherein the implantable electronic device comprises an implantable cardiac monitor.

* * * * *